United States Patent [19]

Martin

[11] Patent Number: 5,322,856

[45] Date of Patent: * Jun. 21, 1994

[54] FORTIFIED GLUTARALDEHYDE CHEMICAL STERILANT/DISINFECTANT

[76] Inventor: Howard Martin, 1106 Spring St., Silver Spring, Md. 20910

[*] Notice: The portion of the term of this patent subsequent to Oct. 12, 2010 has been disclaimed.

[21] Appl. No.: 47,948

[22] Filed: Apr. 16, 1993

Related U.S. Application Data

[63] Continuation-in-part of Ser. No. 468,186, Jan. 22, 1990, Pat. No. 5,252,606.

[51] Int. Cl.$^5$ .............. A61K 31/19; A61K 31/15; A61K 31/11; A61K 31/05
[52] U.S. Cl. ........................... 514/574; 514/643; 514/671; 514/674; 514/698; 514/705; 514/731
[58] Field of Search .............. 514/574, 643, 698, 705, 514/731, 671, 674

[56] References Cited

U.S. PATENT DOCUMENTS

| | | | |
|---|---|---|---|
| 4,764,527 | 8/1988 | Wagner et al. | 514/256 |
| 4,923,899 | 5/1990 | Wachman et al. | 514/642 |

*Primary Examiner*—Zohreh A. Fay

*Attorney, Agent, or Firm*—Walter G. Finch

[57] ABSTRACT

A fortified glutaraldehyde compound with and without dual synergistic phenols is provided for disinfection and sanitization. One formula consists of: glutaraldehyde; dual quaternary ammonium chloride (n-alkyl dimethylethylbenzyl ammonium chloride and n-alkyl dimethylbenzyl ammonium chloride); para tertiary amyl phenol; ortho phenyl phenol; citric or acetic acid; sodium citrate; isopropyl or ethyl alcohol; triethanol amine-HCl; and water in the following proportions: 25.00 to 42.00 grams; 25.00 grams; 1.00 gram; 1.00 gram; 0.50 grams; 0.25 grams; 14.00 grams; 1.00 gram; and 32.25 to 15.25 grams. The formula for environmentally protected uses consists of: glutaraldehyde; dual quaternary ammonium chloride (n-alkyl dimethylethylbenzyl ammonium chloride and n-alkyl dimethylbenzyl ammonium chloride); citric or acetic acid; sodium citrate; isopropyl or ethyl alcohol; triethanol amine-HCl; and water in the following proportions: 25.00 to 42.00 grams; 25.00 grams; 0.50 grams; 0.25 grams; 14.00 grams; 1.00 gram; and 34.25 to 17.25 grams. These formulations are the concentrated formulations and can be diluted for use in the health professions, consumer areas, and agricultural areas.

6 Claims, No Drawings

FORTIFIED GLUTARALDEHYDE CHEMICAL STERILANT/DISINFECTANT

This application is a continuation in part of Ser. No. 07/468,186, filed on Jan. 22, 1990 now U.S. Pat. No. 5,252,606.

BACKGROUND AND SUMMARY OF THE INVENTION

This invention is an improvement over the chemical disinfectant and sterilant composition disclosed in my U.S. Pat. No. 4,469,614 and U.S. Pat. No. 4,654,374 and U.S. patent application Ser. No. 07/468,186 filed Jan. 22, 1990 now U.S. Pat. No. 5,252,606 for Fortified Glutaraldehyde Disinfectant.

| Prior Art Patents | | | |
|---|---|---|---|
| 3,915,877 | 10/1975 | Ware | 252/106 |
| 4,208,404 | 06/1980 | Cowan | 424/153 |
| 4,469,614 | 09/1984 | Martin | 514/705 |
| 4,654,374 | 05/1987 | Martin | 514/698 |

A new and unique combination of various independent biocides has been formulated. Glutaraldehyde in the acidic form has been shown by several investigators, including this inventor, to be superior to the alkaline form of glutaraldehyde in cidal effectiveness.

However, the product has been shown to be erratic in killing effectiveness against mycobacterium tuberculosis, as a sporicide for sterilization, and especially in effectiveness against the polio virus.

The rate of reaction is pH dependent. Acidic glutaraldehyde is more stable than alkaline forms. Solutions above pH 8, which are activated, lose effectiveness within four (4) weeks, while those solutions below a neutral pH (7) can remain active for up to two (2) years. Organic matter does not rapidly diminish the effect of acidic glutaraldehyde in contrast to alkaline glutaraldehyde.

The two phenolics chosen for this combination product are para tertiary amyl phenol and ortho phenyl phenol. The para substitution increases antibacterial activity by increasing surface action. However, it also decreases water solubility. The ortho form increases antibacterial action.

The difficulty in the past has been to maintain these phenolics in an aqueous solution. The new formulation of this invention maintains the phenolics in a solubilized system that has not previously been available.

The ability to maintain the phenolics in acidic solution potentiates their antimicrobial activity. The low pH of this new formulation enables a lower concentration of phenolics to accomplish the equivalent killing effectiveness of higher concentrations used in previous formulations. Phenolics will sometimes be affected by reacting with organic matter. Ortho phenyl phenol is effective against TB, while glutaraldehyde is slow and the quaternary ammonium chloride is only inhibitory.

Quaternary ammonium chloride (QAC) is a cationic surface acting agent. QAC is effective as it penetrates the lipid coating of TB. However, it has been shown in the 1970's to be inactivated be hard water; it is merely inhibitory when used alone.

The QAC's are primarily active against gram positive organisms and require very high concentrations against gram negative organisms. QAC's are not effective against mycobacterium tuberculosis. Viruses are more resistant that bacteria and fungi to the QAC's, which have poor effects against hydrophilic types (enteroviruses, polio, coxsackie, and ECHO).

In addition, QAC's are fungistatic rather than fungicidal. They are greatly affected by organic matter. Depending upon its concentration, phenol will retard or inhibit germination of bacterial spores, as will acidic glutaraldehyde. However, QAC's allow germination to proceed, but inhibit outgrowth. QAC's act on the bacterial cell membrane in a manner similar to hemolysis while phenols promote a concentration-dependent leakage of cell contents from microbial cells.

Alcohols have been shown to have antimicrobial properties. They are fast acting but are poor against spores and viruses. Usually the most effective concentration of the superior alcohols (ethyl alcohol and isopropyl alcohol) is about 60–70%. Ethyl alcohol is popular because of lack of odor and low irritation. Isopropyl alcohol is considered to be more effective against bacteria than ethyl alcohol.

Alcohol is effective against mycobacterium tuberculosis. The isopropyl alcohol bactericidal effectiveness paralleled that of ethyl alcohol but surpassed ethyl alcohol in lower ranges. Either isopropyl of ethyl alcohol may be utilized within the formulation.

The combination of chemicals of the present invention create a synergistic effect that leads to a superior combination. Each part adds a different aspect to cidal effectiveness as well as enhances and creates a superior and more effective chemical sterilant/disinfectant than is achievable by the individual components, the whole combination being more effective than the sum of the individual chemicals.

The particular proportions of the components are important so as to maintain their solubility and ideal effectiveness at the lowest concentrations. The low pH maintained by the citric or acetic acid is another unusual and key feature of the invention. On its own, this combination is bactericidal and its spectrum of activity includes all the common non-sporing pathogens including tubercle bacilli. The ethanol or isopropyl alcohol acts as a solvent to release constituents which leads to bacterial death. It is also virucidal against both hydrophilic and lipophilic viruses.

With this unique combination of ingredients, the ability of the organic matter and the minerals in the water to reduce cidal effectiveness of the glutaraldehyde and QAC is diminished. In addition, the toxic side-effects of the solution are minimized due to the synergism, which effect allows a lower concentration to be used while maintaining higher effectiveness. QAC is effective now at a lower concentration than it would be if utilized alone.

This new biocide formulation is quick acting (less down time to disinfect), has a broad spectrum of biocidal activity, has a detergent property necessary for proper cleansing and penetration, is not corrosive (at use dilution), at use dilution has good skin tolerance, and is easily disposable. The alcohol is held in solution in this formulation by the QAC's, and acts to hold the phenolics in solution. This is an example of synergism, while the glutaraldehyde exerts its bactericidal effect and the phenolics exert their tuberculocidal effects, which thereby enhances the glutaraldehyde and QAC effects.

This new combination of chemicals allows each part to enhance the other for a superior cidal effect. In laboratory testing, this new combination formulation lead to unexpected results that indicate a superior cidal effectiveness at much reduced concentrations, approximately one-half of that previous combinations.

COMPARISON OF THE CIDAL EFFECT OF FORTIFIED Glutaraldehyde WITH DUAL PHENOLICS TO OTHER DISINFECTANTS OF THE SAME GENERAL CATEGORY Time (min.) to Kill Test Organism at Given Dilution of Product
Test Organism

|  | GKN[1] | | | GLUT A[2] | GLUT B[3] |  |
|---|---|---|---|---|---|---|
|  | 1:128 | 1:256 | 1:512 | 1:20 | 1:40 | Undiluted |
| Glutaraldehyde % | 0.20 | 0.10 | 0.05 | 0.50 | 0.25 | 2.0 |
| P. aeruginosa | 2 | 3 | 10 | 5 | 10 | 10 |
| S. aureus | 2 | 3 | 10 | 5 | 10 | 10 |
| S. choleraesuis | 1 | 3 | 10 | 5 | 10 | 10 |
| T. mentagrophytes | 1 | 2 | 10 | 5 | 10 | 10 |
| M. bovis BCG | 3 | 4 | 10 | 10 | 20 | 20 |

[1]GKN - fortified glutaraldehyde with dual chain quaternary ammonium chloride and dual phenolics
[2]GLUT A - dual phenol fortified glutaraldehyde product
[3]GLUT B - conventional 2% alkaline glutaraldehyde product

PHENOL COEFFICIENTS: FORTIFIED GLUTARALDEHYDE WITH DUAL PHENOLICS VS STANDARD PHENOL SOLUTION

| | Phenol Coefficient | | |
|---|---|---|---|
| Test Organism | GKN[1] | GLUT A[2] | GLUT B[3] |
| S. aureus | 8.5 | 1.4 | 0.02 |
| S. choleraesuis | 5.7 | 0.8 | 0.01 |
| P. aeruginosa | 6.4 | 1.0 | 0.01 |
| M. bovis BCG | 10.2 | 0.8 | 0.02 |
| T. mentagrophytes | 7.3 | 0.6 | 0.02 |

[1]GKN - fortified glutaraldehyde with dual quaternary ammonium chloride and dual phenolics
[2]GLUT A - dual phenol fortified glutaraldehyde product
[3]GLUT B - conventional 2% alkaline glutaraldehyde product

COMPARISON OF STERILANT TEST RESULTS FOR FORTIFIED GLUTARALDEHYDE WITH DUAL PHENOLICS VS GLUT A AND GLUT B

Time (hrs) to Kill Test Organism at Given Dilution
Test Organism

|  | GKN[1] | | | GLUT A[2] | GLUT B[3] |  |
|---|---|---|---|---|---|---|
|  | 1:64 | 1:128 | 1:256 | Undil. | 1:20 | Undil. |
| Glutaraldehyde % | 0.40 | 0.20 | 0.10 | 2.00 | 0.50 | 2.00 |
| C. sporogenes | 4 | 10 | 12 | 6 | 12 | 6 |
| B. subtilis | 4 | 8 | 10 | 6 | 12 | 6 |

[1]GKN - fortified glutaraldehyde with dual quaternary ammonium chloride and dual phenolics
[2]GLUT A - dual phenol fortified glutaraldehyde product
[3]GLUT B - conventional 2% alkaline glutaraldehyde product

STUDIES IN AN ULTRASONIC BATH UTILIZING TWO DILUTIONS OF FORTIFIED GLUTARALDEHYDE WITH DUAL PHENOLICS

Time (min) to Kill Test Organisms at Given Dilution
Test Organism

|  | GKN[1] | | GLUT A[2] | |
|---|---|---|---|---|
|  | 1:256 | 1:512 | 1:20 | 1:40 |
| Glutaraldehyde % | 0.10 | 0.05 | 0.50 | 0.25 |
| P. aeruginosa | 1 | 3 | 3 | 5 |
| S. aureus | 1 | 3 | 3 | 5 |
| S. choleraesuis | 1 | 3 | 3 | 5 |
| T. mentagrophytes | 1 | 2 | 3 | 5 |
| M. bovis BCG | 3 | 5 | 5 | 10 |
| C. sporogenes | 30 | 90 | 60 | 120 |

STUDIES IN AN ULTRASONIC BATH UTILIZING TWO DILUTIONS OF FORTIFIED GLUTARALDEHYDE WITH DUAL PHENOLICS -continued Time (min) to Kill Test Organisms at Given Dilution
Test Organism

|  | GKN[1] | | GLUT A[2] | |
|---|---|---|---|---|
|  | 1:256 | 1:512 | 1:20 | 1:40 |
| Glutaraldehyde % | 0.10 | 0.05 | 0.50 | 0.25 |
| B. subtilis | 30 | 60 | 45 | 90 |

[1]GKN - fortified glutaraldehyde with dual chain quaternary ammonium chloride and dual phenolics
[2]GLUT A - dual phenol fortified glutaraldehyde product In field service testing without the phenolics for environmental safety, it was demonstrated that the new formulation was able to penetrate, clean and disinfect an industrial oil well head in one treatment using this single product alone. This is normally accomplished by multiple products.

These unusual results indicate the uniqueness of the formulation: its ability to coalesce and maintain these independent compounds in one solubilized, stable, aqueous solution, this enabled the new superior biocidal compound to be developed.

One of the objects of this invention is to provide a fortified glutaraldehyde compound having unique characteristics.

Another object of this invention is to provide a high fortified glutaraldehyde formulation that can be used effectively and efficiently in industrial, commercial, and agricultural areas to kill sulfate reducing bacteria that are specific to corrosion problems in the oil producing area.

Still another object of this invention is to provide a high fortified glutaraldehyde that can be used in industrial situations requiring cleaning and disinfecting at higher concentrations.

A further object of this invention is to provide a new highly fortified glutaraldehyde formulation that has a broad spectrum of biocidal activity, and can be used in health care areas.

A further object of this invention is to provide a fortified glutaraldehyde formulation that has a detergent property necessary for proper cleansing and penetration.

An additional object of this invention is to provide a high fortified glutaraldehyde formulation which has good skin tolerance and is easily disposable.

To provide a high fortified glutaraldehyde formulation in which the chemicals thereof allow each part to enhance the other for superior cidal effects is still another object of this invention.

These new formulations consist of the following parts by weight and/or percent:

| Fortified Glutaraldehyde Formulas: | WEIGHT | PERCENT |
|---|---|---|
| Glutaraldehyde | 25.00 grams | 25.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Para Tertiary Amyl Phenol | 1.00 gram | 1.00% |
| Ortho Phenyl Phenol | 1.00 gram | 1.00% |
| Citric or Acetic Acid | 0.50 gram | 0.50% |
| Sodium Citrate | 0.25 gram | 0.25% |
| Isopropyl or Ethyl Alcohol | 14.00 grams | 14.00% |
| Triethanol amine-HCl | 1.00 gram | 1.00% |
| Water | 32.25 grams | 32.25% |
| Totals | 100.00 grams | 100.00% |
| Glutaraldehyde | 35.00 grams | 35.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Para Tertiary Amyl Phenol | 1.00 gram | 1.00% |
| Ortho Phenyl Phenol | 1.00 gram | 1.00% |
| Citric or Acetic Acid | 0.50 grams | 0.50% |
| Sodium Citrate | 0.25 grams | 0.25% |
| Isopropyl or Ethyl Alcohol | 14.00 grams | 14.00% |
| Triethanol Amine-HCl | 1.00 gram | 1.00% |
| Water | 22.25 grams | 22.25% |
| Totals | 100.00 grams | 100.00% |
| Glutaraldehyde | 42.00 grams | 42.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Para Tertiary Amyl Phenol | 1.00 gram | 1.00% |
| Ortho Phenyl Phenol | 1.00 gram | 1.00% |
| Citric or Acetic Acid | 0.50 gram | 0.50% |
| Sodium Citrate | 0.25 gram | 0.25% |
| Isopropyl or Ethyl Alcohol | 14.00 grams | 14.00% |
| Triethanol Amine-HCl | 1.00 gram | 1.00% |
| Water | 5.25 grams | 15.25% |
| Totals | 100.00 grams | 100.00% |

| Fortified Glutaraldehyde Without Phenols for Environmental Use: | Weight | Percent |
|---|---|---|
| Glutaraldehyde | 25.00 grams | 25.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Citric or Acetic Acid | 0.50 grams | 0.50% |
| Sodium Citrate | 0.25 grams | 0.25% |
| Isopropyl or Ethyl Alcohol | 14.00 grams | 14.00% |
| Triethanol Amine-HCl | 1.00 gram | 1.00% |
| Water | 34.25 grams | 34.25% |
| Totals | 100.00 grams | 100.00% |
| Glutaraldehyde | 35.00 grams | 35.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Citric or Acetic Acid | 0.50 grams | 0.50% |
| Sodium Citrate | 0.25 grams | 0.25% |
| Isopropyl or Ethyl Alcohol | 14.00 grams | 14.00% |
| Triethanol Amine-HCl | 1.00 gram | 1.00% |
| Water | 24.25 grams | 24.25% |
| Totals | 100.00 grams | 100.00% |
| Glutaraldehyde | 42.00 grams | 42.00% |
| Dual Quaternary Ammonium Chloride (N-alkyl dimethylethylbenzyl ammonium chloride) (N-alkyl dimethylbenzyl ammonium chloride) | 25.00 grams | 25.00% |
| Citric of Acetic Acid | 0.50 grams | 0.50% |
| Sodium Citrate | 0.25 grams | 0.25% |
| Isopropyl or Ethyl Alcohol | 14.00 grams | 14.00% |
| Triethanol Amine-HCl | 1.00 gram | 1.00% |
| Water | 17.25 grams | 17.25% |
| Totals | 100.00 grams | 100.00% |

These formulations have usage in the health field and industrial, agricultural and consumer areas. The formulations may be in the form of an immersion solution, a spray, or a wipe. It may be activated by ultrasound, thermal activity, microwaves, radiation, ultraviolet, or any other energy source for enhancement of effect. The formulations listed above are the concentrated forms. The formulations may be diluted for use.

As can be readily understood from the foregoing description of a high fortified glutaraldehyde formulation, the present structured formulation can be further structured in different modes of formulation to provide an ability to disinfect and sterilize articles, surfaces and the like. A formulation of fortified glutaraldehyde, without phenolics, is shown for specific environmental usage.

Comparison of Biocides at Various Concentrations Allowing 6 Hours of Contact Time Against API Strain SRE (No phenolics)

| Experiment | (ppm) | Bacterial Cells/ml Biocides | | | | |
|---|---|---|---|---|---|---|
| | | GKN-0 | GKN-42% | K-67 | K-54 | Control |
| 1 | 250 | $10^2$ | 10 | 10 | $10^2$ | $10^6$ |
| 2 | 100 | 10 | 10 | ND | $10^2$ | $10^3$ |
| 3 | 400 | $10^2$ | 10 | 0 | ND | $10^{10}$ |
| 4 | 300 | $10^2$ | $10^2$ | $10^3$ | $\geq 10^3$ | $10^{10}$ |
| 5 | 500 | 0 | 0 | 0 | 0 | $10^9$ |
| 6 | 250 | $10^2$ | $10^2$ | $10^2$ | $\geq 10^3$ | $10^8$ |
| 7 | 250 | $10^2$ | $10^2$ | $10^2$ | $\geq 10^3$ | $10^6$ |
| 8 | 300 | $10^2$ | $10^2$ | $10^2$ | ND | $10^9$ |
| | 600 | 0 | 0 | 0 | ND | $10^{10}$ |
| 9 | 300 | $10^2$ | $10^2$ | $10^3$ | $10^4$ | $10^8$ |
| | 400 | 10 | 10 | 10 | ND | $10^{10}$ |

GKN-0 = Fortified Glutaraldehyde at 35%
GKN-42 = Fortified Glutaraldehyde at 42%
K-67 = Glutaraldehyde at 50% - Standards in use
K-54 = Glutaraldehyde at 50% - Standards in use The above tests were performed using the formulation of the fortified glutaraldehyde that does not contain the diol phenolic component for environmental usage.

The above results clearly show the synergistic effect of the formulation.

The use of triethanol amine-HCl counteracts the problem of hard water-dissociation. The triethanol amine-HCl keeps the formulation in solution in the presence of hard water.

The following experiment was performed to test the effectiveness of the fortified glutaraldehyde compound without the phenolics as a disinfectant for cooling tower water using the following protocol of fortified glutaraldehyde at a ratio of 0.000065% glutaraldehyde final concentration in each sample. Treated bacteria sample were taken at set times. Incubated for 48 hours at 37° celsius.

Number of Bacterial Colonies Counted at 48 Hours of Incubation

| Sample Time | Glutaraldehyde Total | Glutaraldehyde Coliform | Glutaraldehyde with phenol Total | Glutaraldehyde with phenol Coliform |
|---|---|---|---|---|
| 0 | 17 | 39 | 10 | 9 |
| 0 | 34 | 22 | 29 | 13 |
| 10 min | 0 | 0 | 1 | 0 |
| 10 min | 0 | 0 | 2 | 1 |
| 90 min | 0 | 0 | 0 | 0 |
| 17.5 hr | 0 | 0 | 0 | 0 |
| Control | + | + | + | + |

+ indicates colonies were present

The function of the acetic or citric acid component is to eliminate any tackiness of the product residue.

Accordingly, modifications and variations to which the formulation is susceptible may be practiced without departing from the scope and intent of the appended claims.

THE EFFECTIVENESS OF THE FORTIFIED GLUTARALDEHYDE COMPOUND AS A DISINFECTING SOLUTION AT AN EXPOSURE TIME OF 3 HOURS

| Test Organism | Exposure Time | Carrier Type | No. of Growths/ Total No. of Tubes |
|---|---|---|---|
| S. choleraesuis | 3 min | SS | 0/180 |
| S. aureus | 3 min | SS | 0/100 |
| P. aeruginosa | 3 min | SS | 0/180 |
| T. mentagrophytes | 3 min | SS | 0/40 |
| M. bovis | 15 min | Logarithmic Reduction Method | |

What is claimed is:

1. A high fortified glutaraldehyde, comprising, a basic formulation of chemical ingredients, said formulation of chemical ingredients consisting of the following quantities of chemical ingredients, said quantities being by weight of the total weight of said basic formulation: glutaraldehyde 25.00 grams; dual quaternary ammonium chloride 25.00 grams, (n-alkyl dimethylethylbenzyl ammonium chloride and n-alkyl dimethylbenzyl ammonium chloride); para tertiary amyl phenol 1.00 gram; ortho phenyl phenol 1.00 gram; citric or acetic acid 0.50 grams; sodium citrate 0.25 grams; isopropyl or ethyl alcohol 14.00 grams; triethanol amine-HCl 1.00 gram; water 32.25 grams, with said formulation of said chemical ingredients being used to form a base stock solution.

2. A high fortified glutaraldehyde, comprising a basic formulation of chemical ingredients, said formulation of chemical ingredients consisting of the following quantities of chemical ingredients, said quantities being by weight of the total weight of said basic formulation: glutaraldehyde 35.00 grams; dual quaternary ammonium chloride 25.00 grams, (n-alkyl dimethylethylbenzyl ammonium chloride and n-alkyl dimethylbenzyl ammonium chloride); para tertiary amyl phenol 1.00 gram; ortho phenyl phenol 1.00 gram; citric or acetic acid 0.50 grams; sodium citrate 0.25 grams; isopropyl or ethyl alcohol 14.00 grams; triethanol amine-HCl 1.00 gram; water 22.25 grams, with said formulation of said chemical ingredients being used to form a base stock solution.

3. A high fortified glutaraldehyde, comprising a basic formulation of chemical ingredients, said formulation of chemical ingredients consisting of the following quantities of chemical ingredients, said quantities being by weight of the total weight of said basic formulation: glutaraldehyde 42.00 grams; dual quaternary ammonium chloride 25.00 grams, (n-alkyl dimethylethylbenzyl ammonium chloride and n-alkyl dimethylbenzyl ammonium chloride); para tertiary amyl phenol 1.00 gram; ortho phenyl phenol 1.00 gram; citric or acetic acid 0.50 grams; sodium citrate 0.25 grams; isopropyl or ethyl alcohol 14.00 grams; triethanol amine-HCl 1.00 gram; water 15.25 grams, with said formulation of said chemical ingredients being used to form a base stock solution.

4. A high fortified glutaraldehyde, comprising a basic formulation of chemical ingredients, said formulation of chemical ingredients consisting of the following quantities of chemical ingredients, said quantities being by weight of the total weight of said basic formulation: glutaraldehyde 25.00 grams; dual quaternary ammonium chloride 25.00 grams (n-alkyl dimethylethylbenzyl ammonium chloride and n-alkyl dimethylbenzyl ammonium chloride); citric or acetic acid 0.50 gram; sodium citrate 0.25 grams; isopropyl or ethyl alcohol 14.00 grams; triethanol amine-HCl 1.00 gram; water 34.25 grams, with said formulation of said chemical ingredients being used to form a base stock solution.

5. A high fortified glutaraldehyde, comprising a basic formulation consisting of the following quantities of chemical ingredients; said quantities being by weight of the total weight of said basic formulation: glutaraldehyde 35.00 grams; dual quaternary ammonium chloride 25.00 grams, (n-alkyl dimethylethylbenzyl ammonium chloride and n-alkyl dimethylbenzyl ammonium chloride), citric or acetic acid 0.50 grams; sodium citrate 0.25 grams; isopropyl or ethyl alcohol 14.00 grams; triethanol amine-HCl 1.00 gram; water 24.25 grams, with said formulation of said chemical ingredients being used to form a base stock solution.

6. A high fortified glutaraldehyde, comprising a basic formulation consisting of the following quantities of chemical ingredients, said quantities being by weight of the total weight of said basic formulation: glutaraldehyde 42.00 grams; dual quaternary ammonium chloride 25.00 grams, (n-alkyl dimethylethylbenzyl ammonium chloride and n-alkyl dimethylbenzyl ammonium chloride); citric or acetic acid 0.50 grams, sodium citrate 0.25 grams; isopropyl or ethyl alcohol 14.00 grams; triethanol amine-HCl 1.00 gram; water 17.25 grams, with said formulation of said chemical ingredients being used to form a base stock solution.

* * * * *